United States Patent
Iwabuchi et al.

(10) Patent No.: US 6,512,227 B2
(45) Date of Patent: Jan. 28, 2003

(54) METHOD AND APPARATUS FOR INSPECTING PATTERNS OF A SEMICONDUCTOR DEVICE WITH AN ELECTRON BEAM

(75) Inventors: Yuko Iwabuchi, Mito (JP); Hideo Todokoro, Nishitama (JP); Hiroyoshi Mori, Hitachinaka (JP); Mitsugu Sato, Hitachinaka (JP); Yasutsugu Usami, Tokyo (JP); Mikio Ichihashi, Kodaira (JP); Satoru Fukuhara, Hitachinaka (JP); Hiroyuki Shinada, Chofu (JP); Yutaka Kaneko, Hachioji (JP); Atsuko Takafuji, Tokyo (JP); Hiroshi Toyama, Hachioji (JP); Katsuya Sugiyama, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/982,965

(22) Filed: Oct. 22, 2001

(65) Prior Publication Data
US 2002/0024021 A1 Feb. 28, 2002

Related U.S. Application Data

(63) Continuation of application No. 09/442,636, filed on Nov. 18, 1999, now abandoned.

(30) Foreign Application Priority Data

Nov. 27, 1998 (JP) .......................................... 10-336863

(51) Int. Cl.$^7$ ........................... G01N 23/00; G21K 7/00
(52) U.S. Cl. ..................................................... 250/310
(58) Field of Search ......................................... 250/310

(56) References Cited

U.S. PATENT DOCUMENTS

| | | | | |
|---|---|---|---|---|
| 5,557,105 A | * | 9/1996 | Honjo et al. ................. | 250/310 |
| 5,780,853 A | * | 7/1998 | Mori et al. .................. | 250/310 |
| 6,184,526 B1 | * | 2/2001 | Kohama et al. ............ | 250/310 |

* cited by examiner

Primary Examiner—John R. Lee
Assistant Examiner—Johnnie L Smith, II
(74) Attorney, Agent, or Firm—Kenyon & Kenyon

(57) ABSTRACT

An object of the present invention is to provide an inspection method using an electron beam and an inspection apparatus therefor, which are capable of enhancing the resolution, improving the inspection speed and reliability, and realizing miniaturization the apparatus. To achieve the above object, according to the present invention, there is provided an inspection method using an electron beam, including the steps of; applying a voltage on a sample via a sample stage; converging an electron beam on the sample; scanning the sample with the converged electron beam and simultaneously, continuously moving the sample stage; detecting charged particles generated from the sample; and detecting a defect on the sample on the basis of the detected charged particles; wherein a distance between the sample and the shield frame is determined on the basis of a critical discharge between the sample stage and the shield frame; coils of at least hexapoles for correcting the shape of an electron beam are provided; the electron beam is deflected for blanking during movement of the sample with the crossover of the electron beam taken as a fulcrum of blanking; or the magnitude of the voltage applied to the sample may be determined depending on the kind of sample.

17 Claims, 15 Drawing Sheets

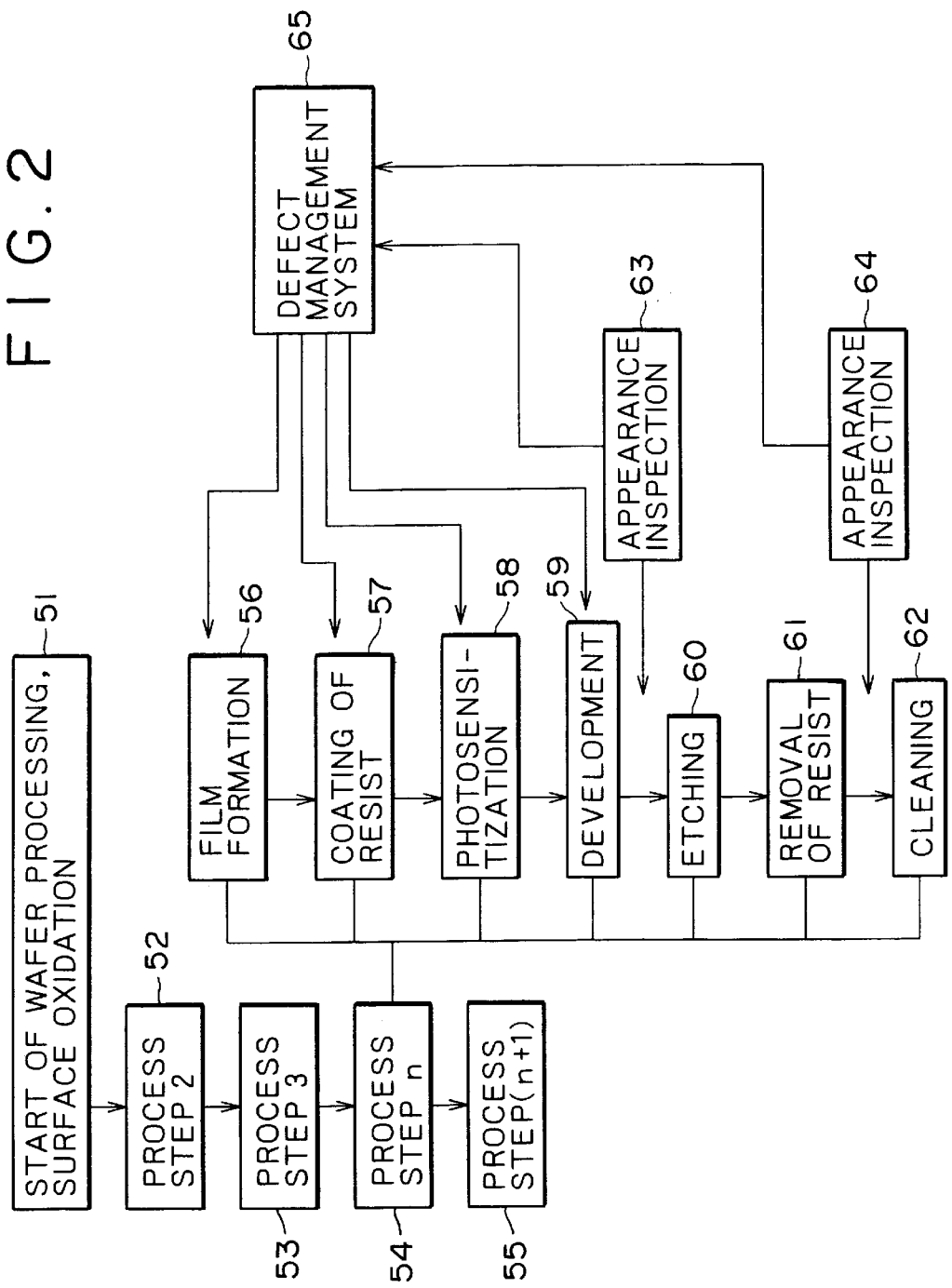

A: ISOLATED DEFECT    E: DISCONNECTION
B: PROJECTION    F: REMAINING THIN FILM
C: SHORT-CIRCUIT    G: OPENING FAILURE
D: LACK

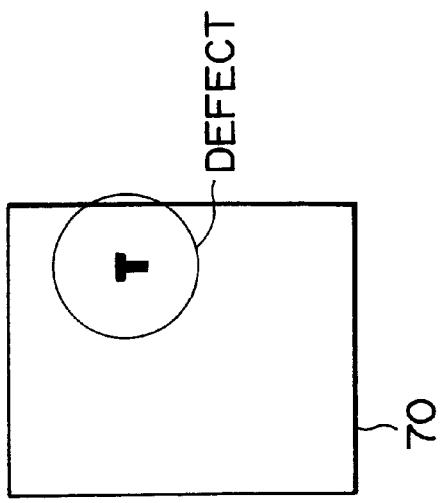
FIG. 10A PICTURE 1
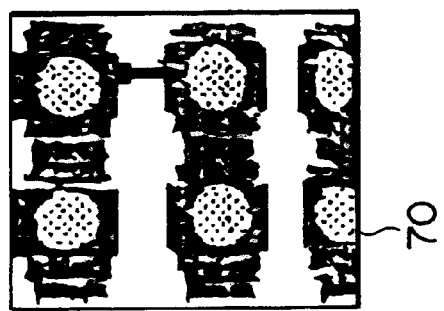
FIG. 10B PICTURE 2
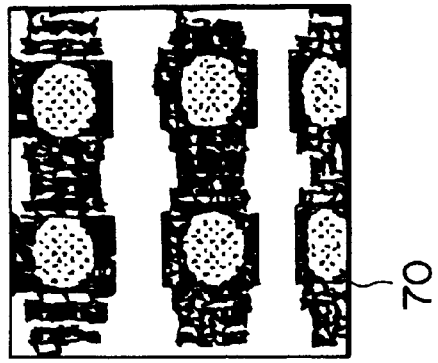
FIG. 10C PICTURE OF DIFFERENCE F I G. 12
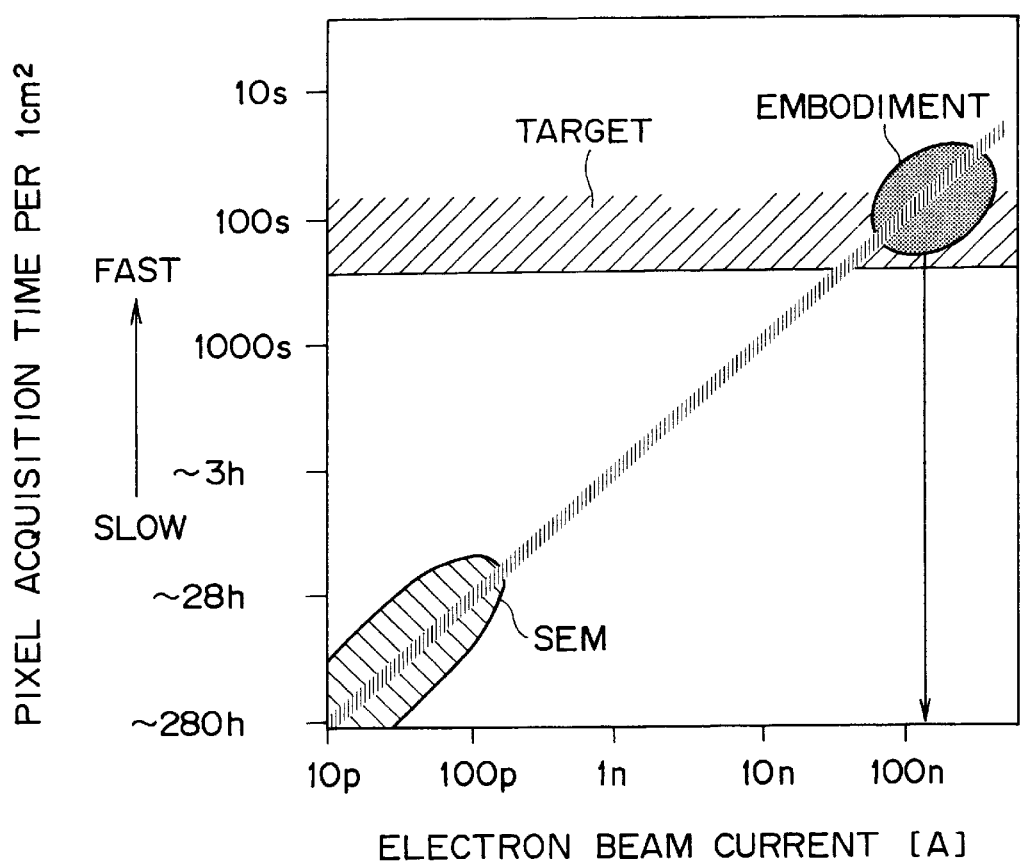

METHOD AND APPARATUS FOR INSPECTING PATTERNS OF A SEMICONDUCTOR DEVICE WITH AN ELECTRON BEAM

This is a continuation of application Ser. No. 09/442,636 filed Nov. 18, 1999 now abandoned.

FIELD OF THE INVENTION

The present invention relates to an inspection method using an electron beam and an inspection apparatus therefor, and particularly to an inspection method using an electron beam and an inspection apparatus therefor, which are suitable for inspecting patterns of circuits, etc. on wafers in the course of fabricating semiconductor devices.

BACKGROUND OF THE INVENTION

As an apparatus for inspecting circuit patterns used for a process of fabricating semiconductor devices, lithography masks, reticles, or the like, there has been known an optical inspection apparatus for detecting a defect on a circuit pattern by irradiating the circuit pattern with light and detecting the reflected light with a CCD or the like. The optical inspection apparatus, however, has a limitation in its resolution, and therefore, as the width of a circuit pattern becomes fine, it is difficult to detect a defect on the pattern by the optical inspection apparatus. Accordingly, an inspection apparatus using an electron beam, which has a high resolution, has come to be used for inspecting a defect on a fine pattern.

As one of apparatuses for observing a sample with an electron beam, there is known a scanning electron microscope (hereinafter, referred to as a "SEM"). Also, as one of apparatuses for inspecting a semiconductor device with an electron beam, there is known a critical dimension scanning electron microscope (hereinafter, referred to as a "CDSEM"). The SEM or CDSEM is suitable for observing a by restricted field of vision at a high magnification; however, it is unsuitable for searching a defect position on a semiconductor wafer. To be more specific, to search a defect position on the semiconductor wafer, it is required to inspect a very wide region, that is, the entire surface region of the semiconductor wafer ranging from 200 mm to 300 mm in diameter, and it takes a lot of time to inspect such a wide region by using the SEM or CDSEM because the electron beam current is low and thereby the scanning speed is low in the SEM or CDSEM. Accordingly, if the SEM or CDSEM is used for inspecting patterns at midway steps of a process of fabricating a semiconductor device, it taken an excessively longer time from the practical viewpoint to inspect the patterns. An inspection apparatus used for inspecting patterns at midway steps of a process of fabricating a semiconductor device is required to speed up the inspection time for increasing the throughput.

An inspection apparatus to solve the above problem has been disclosed, for example, in Japanese Patent Laid-open No. Hei 5-258703, which is configured to detect a defect on a wafer by making use of comparison between images. The inspection apparatus is characterized in (a) using a large electron beam current; (b) continuously moving a sample stage while irradiating a sample or a substrate with an electron beam; (c) using a high acceleration voltage to accelerate an electron beam generated from an electron source; (d) applying a retarding voltage to a sample to decelerate an electron beam, thereby preventing the charging of the sample; and (e) detecting charged particles generated from a sample by irradiation of an electron beam after the charged particles pass through an objective lens, which technique is called a TTL (Through The Lens) type method. The above inspection apparatus makes it possible to more efficiently inspect a defect on a mask or a wafer at a higher speed as compared with the conventional SEM.

In the TTL method, since charged particles generated from a sample are detected after passing through an objective lens, the distance between the objective lens and the sample can be shortened; and also the focal point of the objective lens can be shortened, to reduce aberration of an electron beam, thereby obtaining an image with a high resolution. The TTL method, however, has a non-negligible problem that the rotation of an electron beam largely varies depending on a change in height of a sample, to rotate the obtained image. Accordingly, the TTL method must ensure the accuracy in height of a sample, and therefore, it has a limitation in improvement of the inspecting speed.

The inspection apparatus described in the above document, Japanese patent Laid-open No. Hei 5-258703 adopts a collimated beam for avoiding dimness of the focal point due to Coulomb repulsive interaction of electrons in an electron beam. The adoption of such a collimated beam, however, causes a problem. When a collimated beam is blanked during movement of a sample on a sample stage, part of the collimated beam is not shielded by a stop disposed in a midway point of the trajectory of the electron beam during blanking, whereby a region not required to be irradiated, which is adjacent to a region required to be irradiated, is irradiated with the part of the collimated beam not shield. This results in a possibility that the obtained image is different from the actual one.

FIG. 14 shows a relationship between a retarding voltage and an efficiency of detecting secondary electrons, which is obtained by using a wafer as a sample in a process of fabricating a semiconductor device. In the TTL method shown by (2) in FIG. 14, there occurs a problem that as the retarding voltage is reduced, the efficiency of detecting secondary electrons becomes as low as not to be non-negligible. In the TTL method, secondary electrons generated from a sample are converged through a magnetic field in an objective lens, and the main reason why the efficiency of detecting secondary electrons becomes low as the retarding voltage is reduced is that when the retarding voltage is changed, the irradiation energy given from the electron beam to the sample is changed, with a result that the converged positions of secondary electrons in the axial direction are changed.

To prevent the reduction in efficiency of detecting secondary electrons, it may be considered to increase the retarding voltage; however, if the retarding voltage is increased, since the retarding voltage is applied to a sample stage and a shield frame which surround the end portion of the sample stage is earthed, a discharge occurs between the end portion of the sample stage and the shield frame. This causes an inconvenience in reducing the effect of applying the retarding voltage, or making unstable the electron beam due to occurrence of noise.

Further, since the ease of charge of the sample is dependent on the material of the sample, the magnitude of the retarding voltage must be changed depending on the ease of charge of the kind of sample.

With respect to the irradiation position of an electron beam, the position of a sample stage on which a sample is mounted is accurately measured, and the irradiation position of the electron beam is determined on the basis of the position of the sample stage. An interferometer using a laser beam is provided to measure the position of the sample stage, wherein a laser beam is made incident on mirrors mounted on the sample stage and a minutely changed amount of the position of the sample stage is measured on the basis of the interference of the reflected laser beam. On the other hand, the retarding voltage is applied to the sample via the sample stage on which the sample is mounted, and accordingly, the retarding voltage is also applied to the mirrors mounted to the end portions on two sides of the sample stage. In this case, since the mirror is made from glass, an electric field is concentrated at the end portion of the mirror. As a result, there is a possibility that a discharge occurs between the mirror and another member such as a shield frame provided in proximity to the mirror and earthed. If the mirror is not made from glass, there may occur a discharge between an edge of the mirror made from metal and said another member.

Accordingly, it is required to take into account not only a discharge between the end portion of the sample stage to which the retarding voltage is applied and the shield frame surrounding the sample stage but also the concentration of an electric field at the end portion of the mirror provided for measuring the position of the sample stage.

The above-described discharge phenomenon occurring between the sample stage to which the high retarding voltage is applied and the shield frame can be prevented by sufficiently increasing a distance between the sample stage and the shield frame; however, the increased distance therebetween leads to an increase in the size of the apparatus. In a process of fabricating a semiconductor device, a fabrication apparatus and an inspection apparatus must be disposed in a clean room, and the investment in plant and equipment becomes large in proportional to the floor area of the clean room. From this viewpoint, the inspection apparatus used in the clean room is required not only to realize a higher inspection speed but also to realize space saving by miniaturization.

On the other hand, in the above-described inspection apparatus using an electron beam, as a result of increasing the resolution thereof, the shape in transverse cross-section of the electron beam emitted on a sample may become not a circular shape but a triangular shape with its corners rounded. For example, when a circular-shaped sample is scanned by the triangular-shaped beam, the image on a monitor will be triangular in shape. For another example, when a beam size nearly equals a size of a pixel of the image on the monitor, a foot of the triangular-shaped beam expands the next pixels. That is, the triangular-shaped beam shades off compared with the circular-shaped beam. The above-described inspection apparatus using an electron beam is configured to compare an image derived from a pattern at one location with an image derived from the same pattern at a different location and detect a difference between the two images as an abnormality or a defect. If the shape of the beam is triangular causing expanding, a defect in a fine pattern will not be detected.

The cause of making triangular the shape in transverse cross-section of an electron beam may be considered as follows: namely, since a chip of an electron source, an extraction electrode, a converging lens, and the like are not axisymmetric, the electron beam itself generated from an electron gun becomes triangular; and the electron beam becomes triangular by a converging lens of an optoelectronic system. Accordingly, even by use of an electron beam allowing a high resolution, if there occur the above-described inconveniences, it is impossible to obtain an accurate inspection result.

SUMMARY OF THE INVENTION

An object of the present invention is to provide an inspection method using an electron beam and an inspection apparatus therefor, which are capable of enhancing the resolution, improving the inspection speed and reliability, and realizing miniaturization the apparatus.

To achieve the above object, according to the present invention, there is provided an inspection method using an electron beam, including the steps of; applying a voltage on a sample via a sample stage; converging an electron beam on the sample; scanning the sample with the converged electron beam and simultaneously, continuously moving the sample stage; detecting charged particles generated from the sample; and detecting a defect on the sample on the basis of the detected charged particles; wherein a distance between the sample and the shield frame is determined on the basis of a critical discharge between the sample stage and the shield frame. According to the present invention, there is also provided an inspection apparatus used for the above inspection method. In the above method and apparatus, preferably, coils of at least hexapoles for correcting the shape of an electron beam may be provided; the electron beam may be deflected for blanking during movement of the sample with the crossover of the electron beam taken as a fulcrum of blanking; or the magnitude of the voltage applied to the sample may be determined depending on the kind of sample.

BRIEF DESCRIPTION OF THE DRAWINGS

FIG. 2 is a block diagram showing a procedure of a general process of fabricating a semiconductor device;

FIGS. 10A, 10B and 10C are diagrams of images showing one example of a comparison between the images;

FIG. 12 is a graph showing a relationship between an image acquisition time per 1 $cm^2$ on the surface of a sample and an electron beam current;

DETAILED DESCRIPTION OF THE PREFERRED EMBODIMENTS

Hereinafter, embodiments of the present invention will be described with reference to the drawings. FIG. 2 is a block diagram showing the procedure of a process of fabricating a semiconductor device. As is apparent from FIG. 2, a semiconductor device is fabricated by repeating a large number of steps 51 to 55 of forming patterns on a semiconductor wafer. Each pattern formation step generally includes a film formation step 56, a resist coating step 57, a photosensitization step 58, a development step 59, an etching step 60, a resist removing step 61, and a cleaning step 62. If a fabricating condition is not optimized at each step, a circuit pattern of a semiconductor wafer is not normally formed.

To keep the optimization of the fabricating condition at each step, an appearance inspection step 63 or 64 is provided between the steps for carrying out the inspection of the circuit pattern. If a defect is found at the appearance inspection step 63 or 64, the inspection result is fed back to the step at which the process containing a cause of occurrence of the defect has been carried out, to thereby suppress repetition of occurrence of the same defect. The feedback of the inspection result is performed by a defect management system 65 shown in FIG. 2. To be more specific, data is fed to fabrication apparatuses at the steps 56, 57, 58 and 59 by the defect management system 65. In this case, the fabricating condition can be automatically changed by the defect management system 65.

Figure 3A:
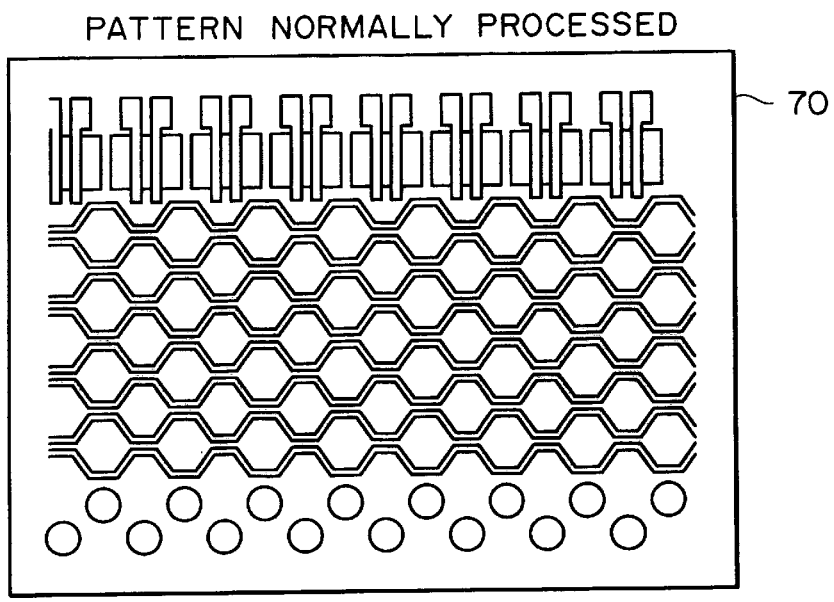
FIGS. 3A and 3B each showing an image obtained, by using a SEM, from a circuit pattern on a semiconductor wafer in the course of fabricating the semiconductor wafer.
Figure 3B:
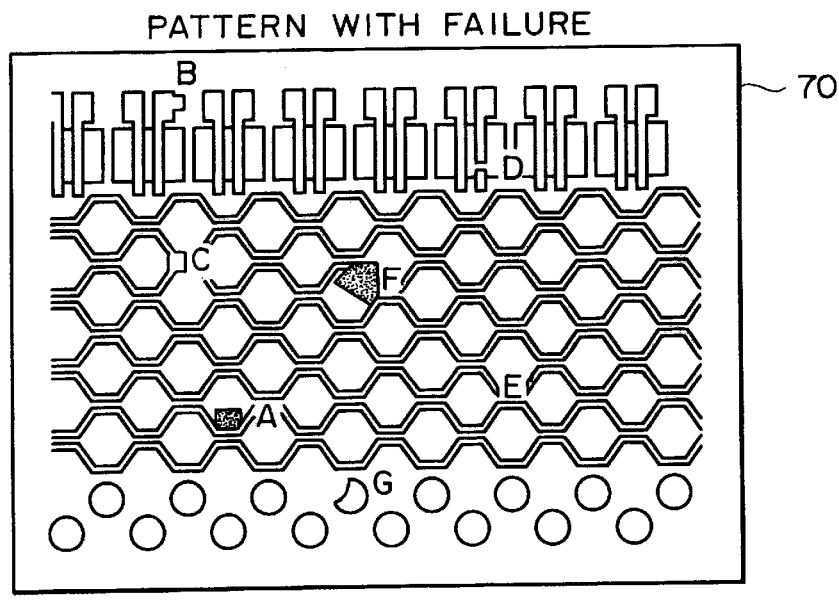

FIGS. 3A and 3B each show an observation image 70 obtained from a circuit pattern of a semiconductor wafer at a certain fabrication step by a scanning electron microscope (SEM). FIG. 3A shows a normally processed pattern, and FIG. 3B shows a pattern with a processing failure. If an abnormality occurs at the film formation step 56 shown in FIG. 2, particles adhere on the surface of the semiconductor wafer, to cause an isolated defect A shown in FIG. 3B. If conditions of focusing, exposure time and the like are not optimized upon photosensitization after resist coating, the amount and intensity of light for iirradiation of the resist become excessive or deficient, to cause a short-circuit C, a disconnection E, and a lack D (or thinned portion of pattern). If a defect appears on a mask or a reticle upon exposure, the same abnormality of the pattern shape as described above is easy to occur.

If an etching amount is not optimized or a thin film or particles generated during etching remain, not only the short-circuit C, a projection B, and the isolated defect A but also an opening failure G occurs. At the cleaning step, abnormal oxidation is easy to occur at a corner, etc. of the pattern depending on the cutwater condition upon drying and also a remaining thin film F difficult to be observed by an optical microscope occurs.

Accordingly, in the wafer fabricating process, it is required to optimize the processing condition in such a manner as to prevent occurrence of the above failure and also it is required to early inspect occurrence of abnormality and feed the inspection result back to the associated step.

To detect the above-described defects, as shown in FIG. 2, the appearance inspection step 63 is provided after the development step 59 and the appearance inspection step 64 is provided after the resist removing step 61. An inspection apparatus using an electron beam according to the present invention is used for inspection at the appearance steps 63 and 64.

Figure 1:
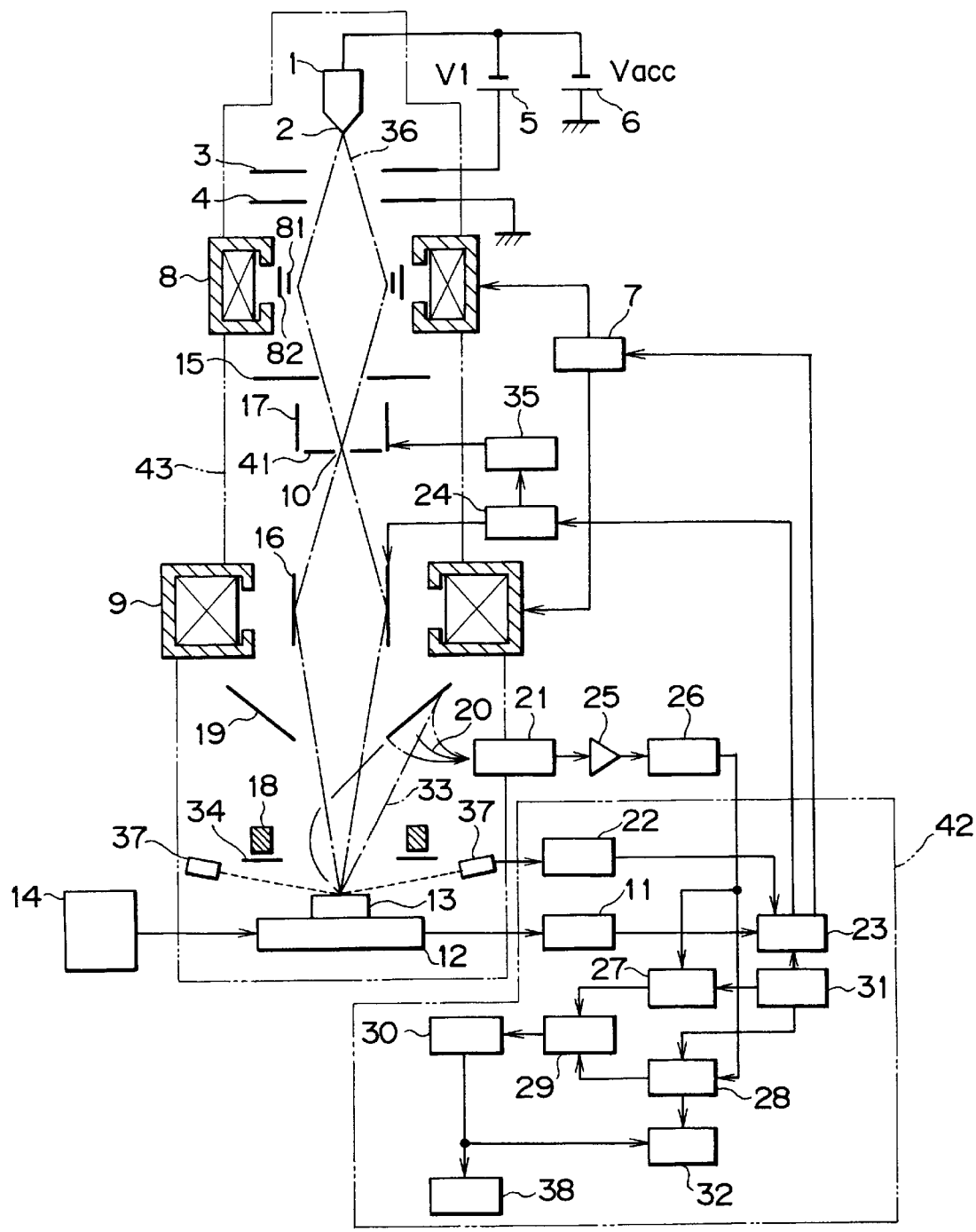
FIG. 1 is a vertical sectional view schematically showing the configuration of an inspection apparatus using an electron beam according to one embodiment of the present invention.

FIG. 1 is a vertical sectional view schematically showing the configuration of an inspecting apparatus using an electron beam according to an embodiment of the present invention.

Referring to FIG. 1, an electron gun 1 is composed of an electron source 2, an extraction electrode 3 and an acceleration electrode 4. An extraction voltage V1 is applied between the electron source 2 and the extraction electrode 3 by an extraction power supply 5, to extract an electron beam 36 from the electron source 2. The acceleration electrode 4 is kept at an earth potential, and an acceleration voltage Vacc is applied between the acceleration electrode 4 and the electron source 2 by an acceleration power supply 6. Accordingly, the electron beam 36 is accelerated with the acceleration voltage Vacc.

The electron beam thus accelerated is converged by a first converging lens 8 connected to a lens power supply 7 in such a manner that a crossover 10 is formed between the first converging lens 8 and an objective lens 9 as a second converging lens connected to the lens power supply 7. The accelerated electron beam is then converged by the objective lens 9 on a sample 13 typically a semiconductor wafer mounted on a sample stage 12 horizontally movable by a stage drive unit (not shown) and a position monitoring/critical dimension measuring device 11. In this way, the sample 13 is irradiated with the electron beam converged thereon. The above configuration is contained in a chamber 43 kept in vacuum atmosphere suitable for irradiation of an electron beam.

A negative voltage as a retarding voltage for decelerating the electron beam 36 is applied to the sample 13 via the sample stage 12 by a variable deceleration power supply 14, and a voltage positive with respect to the sample 13 is applied to an electrode 34 provided between the sample 13 and the objective lens 9. The electron beam 36 is thus decelerated with the retarding voltage. In general, the electrode 34 is kept at an earth potential, and the retarding voltage can be arbitrarily changed by adjusting the variable deceleration power supply 14.

A stop 15 is disposed between the first converging lens 8 and the crossover 10, and a stop 41 is disposed between the crossover 10 and an electron beam scanning deflector 16. These stops 15 and 41 are useful to cut off excessive electrons and to determine the opening angle of the electron beam 36.

The electron beam scanning deflector 16, which is disposed between the crossover 10 and the objective lens 9, functions to deflect the converged electron beam 36 in such a manner that the sample 13 is scanned with the electron beam 36. To be more specific, the electron scanning deflector 16 is provided in the objective lens 9 in such a manner that the fulcrum of deflection substantially corresponds to the center of the magnetic pole gap of the objective lens 9, to thereby reduce the deflection distortion.

A blanking deflector 17, connected to a scanning signal generator 24, for blanking the electron beam 36 by deflecting it at a position where the crossover 10 is formed, is disposed between the stop 15 and an electron beam scanning deflector 16.

Astigmatism correcting coils 81 and 82 having poles of the number of six or more are provided inside the converging lens 8. If the electron source 2, the extraction electrode 3, converging lens, and the like are not axisymmetric, the shape in transverse cross-section of an electron beam emitted to irradiate the sample 13 may become not a circular shape but a triangular shape. The triangular shape of the electron beam is corrected into a circular shape by the astigmatism correcting coils 81 and 82 provided inside the converging lens 8. Such correction of the shape of the electron beam is advantageous in enhancing the resolution. Defects in a fine pattern will be detected.

Figure 4:
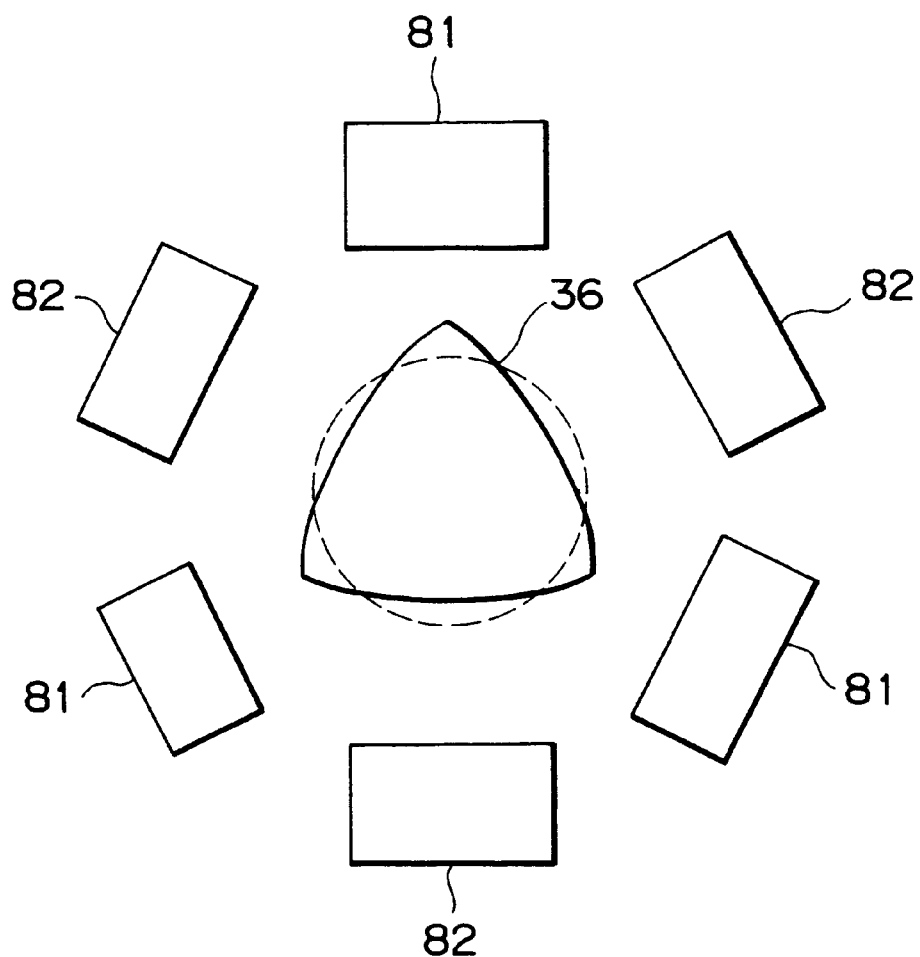
FIG. 4 is a plan view showing arrangement of astigmatism correcting coils.

FIG. 4 is a plan view showing arrangement of the astigmatism correcting coils 81 and 82. When configured as quadrupoles, the astigmatism correcting coils 81 and 82 apply forces to an electron beam in such a manner as to extend the electron beam in the X direction and contract it in the Y direction. If the electron beam has a triangular shape, the triangular shape is not corrected into a circular shape by the shape correction in the X and Y directions. Meanwhile, when configured as hexapoles as shown in FIG. 4, the astigmatism correcting coils 81 and 82 can apply forces to the triangular electron beam in such a manner as to extend three sides of the triangular shape and contract three vertexes of the triangular shape, to thereby correct the triangular shape into a circular shape. The larger the number of poles of the astigmatism correcting coils 81 and 82, the more the accuracy of shape correction of an electron beam into a circular shape; however, actually, the number of poles is determined under the balance of forces generated from the coils against the size of a space containing the coils.

Figure 5:
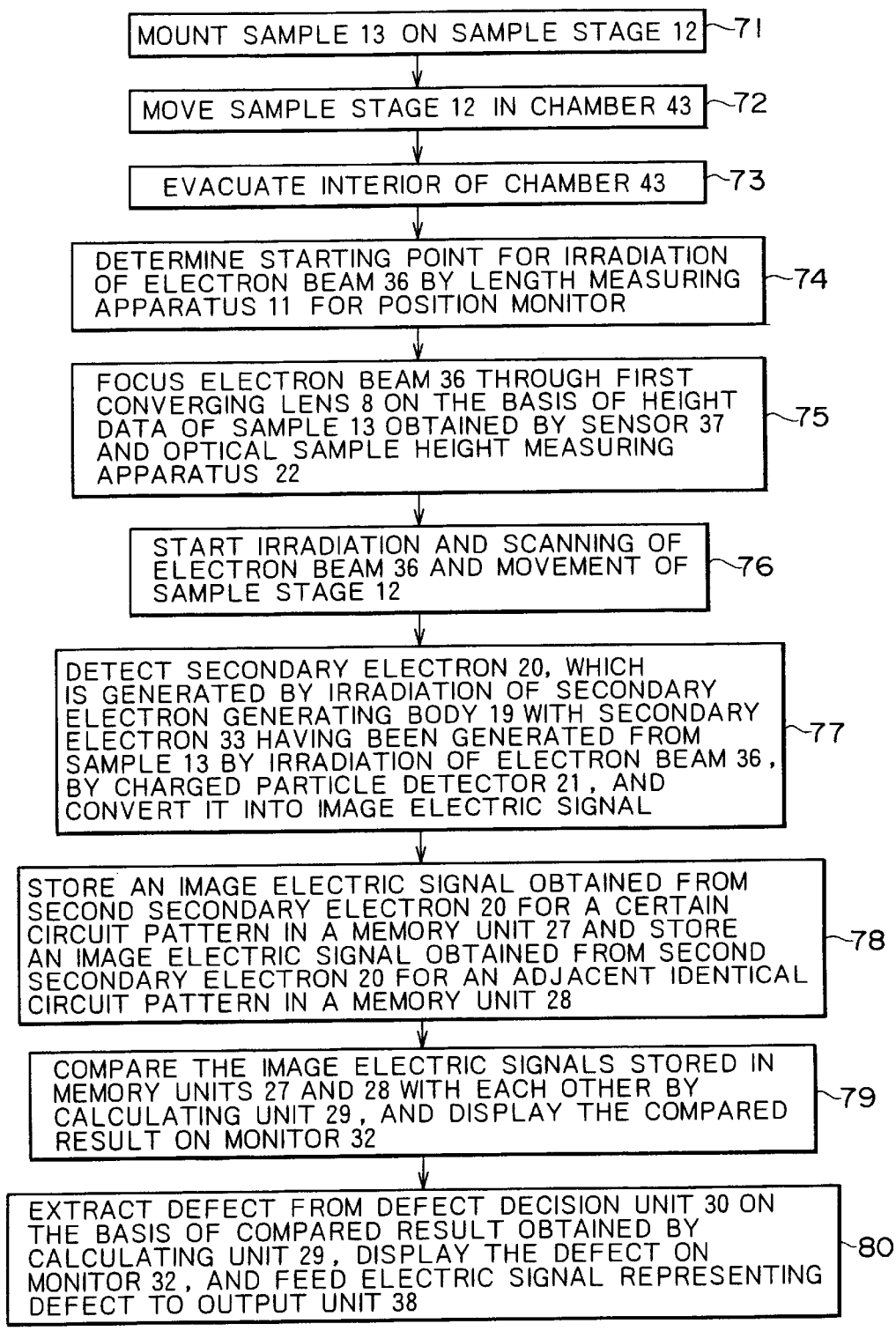
FIG. 5 is a flow chart showing a procedure of inspecting a circuit pattern formed on a semiconductor wafer.

FIG. 5 is a flow chart showing a procedure of inspecting a circuit pattern formed on a semiconductor wafer by using the inspection apparatus of the present invention.

The sample 13 is mounted on the sample stage 12, and the sample stage 12 is moved in a chamber 41. A sample inspection room in the chamber 41 is evacuated, and a retarding voltage is applied to the sample 13 via the sample stage 12.

When the sample 13 is scanned with the converged electron beam 36, secondary electrons 33 as charged particles and reflected electrons are generated from the sample 13. The secondary electrons 33 are defined as electrons having an energy of 50 eV or less.

The retarding voltage applied against the electron beam 36 for irradiation of the sample 13 has a polarity opposed to that of the secondary electrons 33 generated from the sample 13, and therefore, it acts an acceleration voltage for accelerating the secondary electrons 33. The secondary electrons 33 generated from the sample 13 are thus accelerated with the retarding voltage to be substantially arranged in direction and thereby substantially collimated. The substantially collimated beam of the secondary electron electrons 33 is made incident on an EXB (E-cross-B) deflector 18 disposed between the sample 13 and the objective lens 9.

The EXB deflector 18, which is of a type known as a Wien filter, includes a deflection electric field generator for generating a deflection electric field acting to deflect the secondary electrons 33 and also includes a deflection magnetic field generator for generating a deflection magnetic field which is perpendicular to the above deflection electric field for canceling the deflection of the electron beam emitted to irradiated the sample 13 by the above deflection electric field. The deflection magnetic field acts to deflect the secondary electrons 33 in the same direction as the deflection direction by the deflection electric field. Accordingly, the deflection electric field and the deflection magnetic field generated by the EXB deflector 18 act to deflect the accelerated secondary electrons 33 without exerting adverse effect on the electron beam emitted to irradiate the sample 13.

To keep the deflection angle at a nearly constant value, the deflection electric field and the deflection magnetic field generated by the EXB deflector 18 can be changed in linkage of a change in retarding voltage. The EXB deflector 18, which generate the deflection electric field and the deflection magnetic field, is sometimes called a deflection electric field/deflection magnetic field generator.

The secondary electrons 33 deflected by the deflection electric field and the deflection magnetic field generated from the EXB deflector 18 are bombarded with (or flied to irradiate) a conductive secondary electron generator 19. The secondary electron generator 19 is disposed between the objective lens 9 and the EXB deflector 18 in such a manner as to surround the axis of the electron beam. The secondary electron generator 19 is formed into a conical shape which is gradually spread in the axial direction toward the electron gun 1. The secondary electron generator 19 is made from CuBeO and has an ability of generating secondary electrons in the number being about five times the number of the electrons incident thereon. Secondary electrons 20 (having an energy of 50 eV or less) generated from the secondary electron generator 19 are detected by a charged particle detector 21 to be converted into an electric signal.

The height of the sample 13 is measured in real time by an optical sample height measuring device 22, and the measurement result is fed back to the lens power supply 7 via a correction control circuit 23. The focal distance of the objective lens 9 is dynamically corrected on the basis of the measured result. The irradiation position of the electron beam on the sample is detected by the position monitoring/critical dimension measuring device 11, and the measured result is fed back to the scanning signal generator 24 via the correction control circuit 23. The irradiation position of the electron beam on the sample is thus controlled on the basis of the measured result.

Figure 6:
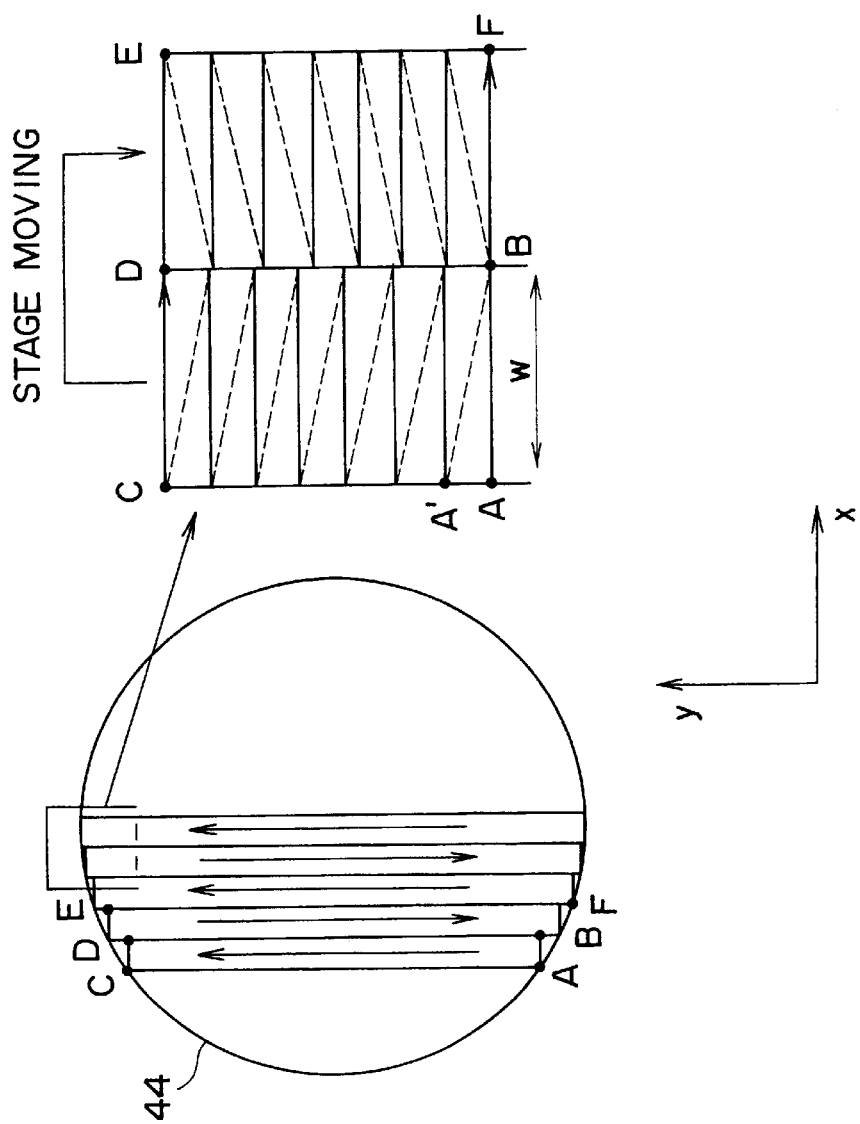
FIG. 6 is a plan view, seen from top, of a wafer.
Figure 7:
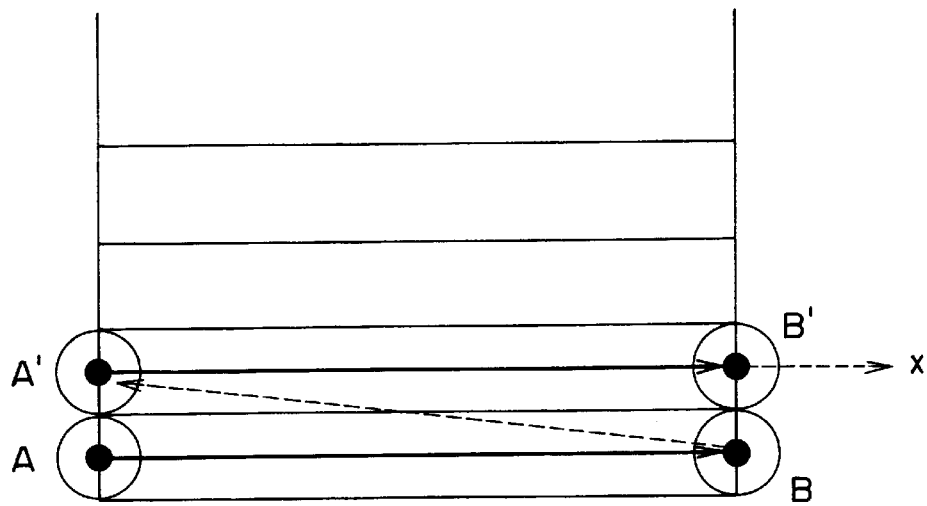
FIG. 7 is an enlarged view showing part of the wafer shown in FIG. 6.

FIG. 6 is a plan view, seen from top, of a semiconductor wafer taken as one example of the sample 13; and FIG. 7 is an enlarged view showing part of the semiconductor wafer 44. The wafer 44 is continuously moved, as shown by an arrow y, in the direction y of x-y coordinates by the stage drive unit (not shown). On the other hand, the wafer 44 is scanned with the electron beam 36 in the direction x. In this case, the scanning and deflection for blanking are alternately repeated as shown by an arrow x during movement of the wafer 44.

To equalize irradiation of the wafer 44 with the electron beam 36 temporally and spatially, the electron beam 36 is deflected for blanking by the blanking defector 17 shown in FIG. 1 for preventing the electron beam 36 from being directed to the wafer 44 during a blanking period of each scanning.

The scanning of the wafer 44 with the electron beam 36 is performed from a starting point A to a point B shown in FIG. 6. During this scanning, the wafer 44 is moved together with the sample stage 12 in the direction y. The electron beam 36 is blanked between the point B and a point A' as shown by the broken line in FIG. 7, and then the scanning is started from the point A' to a point B'. In this way, the scanning and blanking are alternately repeated during movement of the wafer 44 until the scanning between a point C and a point D.

After completion of continuous movement of the wafer 44 from the starting point A to the end point D, the wafer 44 is moved in the direction x by an amount equivalent to a scanning width w by the electron beam 36, and continuous movement of the wafer 44 in the direction -y is re-started from the new starting point D to an end point F. During this continuous movement of the wafer 44, the scanning of the wafer 44 with the electron beam 36 and the blanking of the electron beam 36 are alternately repeated.

By repeating the above operation, the scanning of the entire surface of the wafer 44 with the electron beam 36 is completed.

Figure 8A:
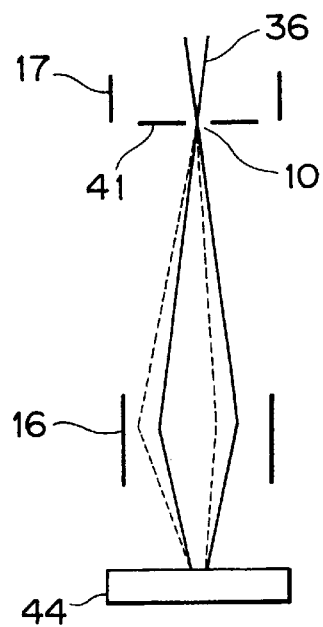
FIGS. 8A and 8B are conceptional diagrams showing the forms of blanking of an electron beam.
Figure 8B:
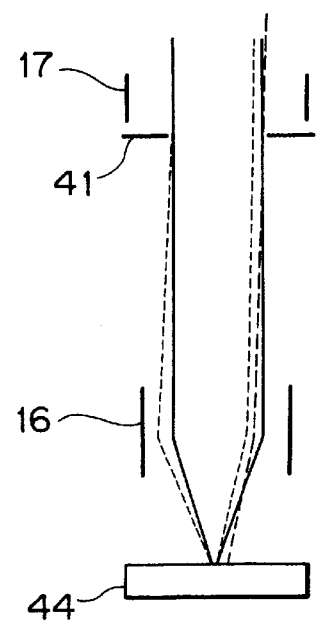

FIGS. 8A and 8B are conceptional diagrams showing the forms of blanking of the electron beam 36 shown in FIG. 71. In this embodiment, the deflection of the electron beam 36 for blanking is performed around the crossover 10 of the electron beam 36 shown in FIG. 1. This is shown in FIG. 8A. If the electron beam 36 is deflected for blanking around a point other than the crossover 10, the irradiation position of the electron beam on the wafer 44 is moved upon the deflection for blanking. Also as shown in FIG. 8B, if the electron beam 36 is a collimated beam, when the electron beam 36 is deflected for blanking, part of the. electron beam 36 is not shield by the stops 15 and 41 during the blanking, with a result that a region not required to be irradiated, which is adjacent to a region required to be irradiated, is slightly irradiated with the part of the electron beam 36. In particular, in the case of enhancing the resolution, the irradiation of the region not required to be irradiated with part of the electron beam 36 causes a problem that an erroneous image is acquired.

On the contrary, in this embodiment, since the electron beam 36 is deflected for blanking around the crossover 10, a region not required to be irradiated, which is adjacent to a region required to be irradiated, is not irradiated with part of the electron beam 36. This makes it possible to avoid the change in irradiation position of the electron beam on the wafer 44, and defects will be detected at high accuracy.

The scanning of the wafer 44 as the example of the sample 13 with the electron beam 36 is performed by deflecting the electron beam 36 in the direction x while continuously moving the wafer 44 in the direction y. In this case, the scanning of the electron beam 36 may be performed by deflecting the electron beam 36 in the forward direction and the backward direction in place of alternately repetition of scanning and deflection for blanking. With this configuration, it is possible to eliminate the necessity of provision of the blanking deflector 17 and to save the blanking time. In this case, however, it is required to take into account the following point.

Figure 9:
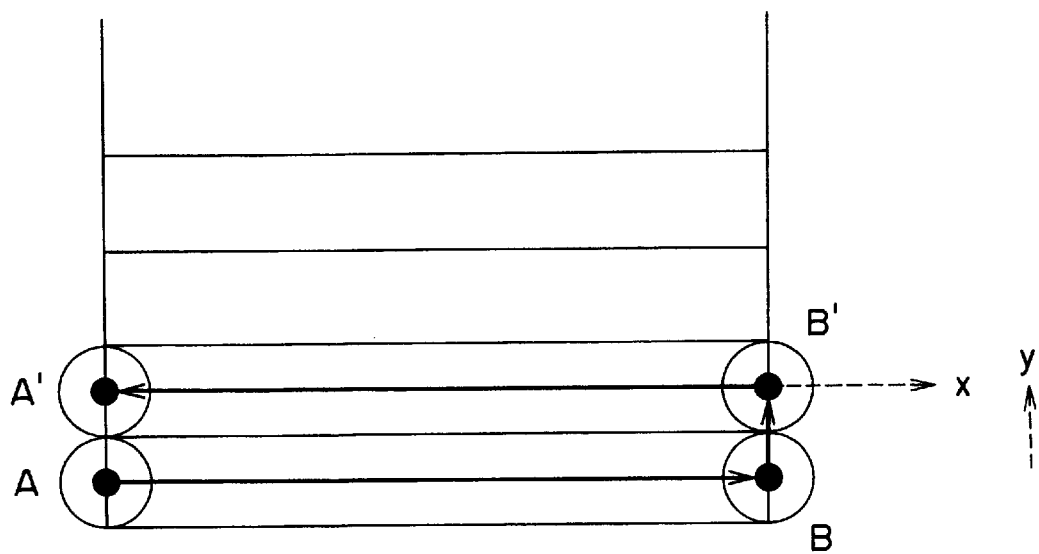
FIG. 9 is an enlarged view, similar to FIG. 7, showing part of the wafer.

FIG. 9 is an enlarged view, similar to FIG. 7, of part of the wafer 44 showing the scanning direction of the electron beam 36 on the wafer 44. Referring to FIG. 9, an end point B of the wafer 44 in the forward deflection of the electron beam 36 and a starting point B' in the backward deflection of the electron beam 36 are concentratedly irradiated with the electron beam 36 for a short time. To be more specific, in the case of scanning in the direction x from left to right, at the end portion B in the irradiation region, the movement of the electron beam in the direction x is stopped, and after the wafer 44 is moved in the direction y by a scanning width to the starting point B', the scanning is re-started in the direction x from right and left. During the period in which the wafer 44 is moved in the direction y from the point B to the point B', an area between a region around the end point B and a region around the point B' is continuously irradiated with the electron beam 36 in the direction y. Accordingly, for a sample in which a time constant of the charging phenomenon is very short, the brightness of the acquired image becomes inhomogeneous. To nearly equalize the irradiated amount by the electron beam 36 over the entire surface of the wafer 44, the scanning speed of the electron beam 36 may be controlled such that the scanning speed between the points B and B' shown in FIG. 9 is faster than that between the points A and B shown in FIG. 9.

Next, the image processing performed by an image processing unit 42 shown in FIG. 1 will be described.

The image processing unit 42 detects a defect on the sample 13 on the basis of an electric signal supplied from the charged particle detector 21. The electric signal, which has been converted from the amount of the secondary electrons 20 by the charged particle detector 21, is amplified by an amplifier 25, and is converted into a digital signal by an A/D converter 26. The digital signal is stored as an image signal in memories 27 and 28. To be more specific, a secondary electron image signal in a first inspection region is stored in the memory 27.

Subsequently, a secondary electron image signal in a second inspection region, adjacent to the first inspection region, of the same circuit pattern is stored in the memory 28 and simultaneously compared with the secondary electron image signal in the first inspection region stored in the memory 27. Further, a secondary electron image signal in a third inspection region is overwritten/stored in the memory 27 and simultaneously compared with the secondary electron image signal in the second inspection-region stored in the memory 28. Such an operation is repeated, to carry out the storage and comparison between two of the image signals over the all inspection regions. In addition, the image signal stored in the memory 28 is displayed on a monitor 32.

The comparison between images is carried out by a calculating unit 29 and a defect decision unit 30 shown in FIG. 1. To be more specific, with respect to the secondary electron image signal stored in the memories 27 and 28, the calculating unit 29 calculates various statistic amounts, specifically, statistic amounts such as an average, a variance, etc. of image concentration values, differential value between peripheral pixels, and the like on the basis of a defect decision condition having been already stored in the calculating unit 29. The image signals thus processed by the calculating unit 29 are transmitted to the defect decision unit 30. The defect decision unit 30 compares the image signals with each other to extract a differential signal, and decides whether or not the differential signal is a defect signal or a non-defect signal on the basis of a defect decision condition having been already stored in the defect decision unit 30.

FIGS. 10A, 10B and 10C are views illustrating one example of comparison between images by using images 70, wherein FIG. 10A shows a secondary electron image signal stored in the memory 27; FIG. 10B shows a secondary electron image signal stored in the memory 28; and FIG. 10C shows a difference between a picture image 1 shown in FIG. 10A and the picture image 2 shown in FIG. 10B. The difference between the picture images shown in FIG. 10C is displayed as a defect.

Further, there may be adopted a method in which a secondary electron image signal in an inspection region of a standard circuit pattern is previously stored in the memory 27, and a secondary electron image signal in an inspection region of a circuit pattern of the sample 13 is stored in the memory 29 and is compared with the image signal stored in the memory 27. To be more specific, an inspection region and an inspection condition of a non-defective semiconductor device are previously inputted from a control unit 31; the non-defective semiconductor device is inspected on the basis of the data thus inputted; and a secondary electron image in a desired region of the non-defective semiconductor device is taken and stored in the memory 27. Next, the inspection for the sample 13 to be inspected is performed in the same manner as described above, and a secondary electron image of the sample 13 is taken and stored in the memory 28 and is simultaneously aligned to and compared with the secondary electron image stored in the memory 27, to detect only a defect.

In this case, as the non-defective semiconductor device, a non-defective portion of the sample 13 or a non-defective wafer or chip different from the sample 13 is used. For example, in the case of forming a circuit pattern on the sample 13, there may occur as a defect composed of misalignment between a lower layer pattern and an upper layer pattern. Such a defect occurring over the entire wafer cannot be detected by comparison between images derived from circuit patterns on the same wafer or chip; however, it can be detected by comparison between an image previously derived from a non-defective and an image derived from the sample 13.

An operational instruction and a condition set-up are supplied from the control unit 31 shown in FIG. 1 to respective inspection apparatuses. Accordingly, various conditions such as an acceleration voltage, a defection width (or scanning width) and a defection speed (or scanning speed) of an electron beam, a moving speed of a sample stage, and a timing of receiving an output signal from a detector are previously inputted in the control unit 31.

Next, a difference between the inspection apparatus using an electron beam according to the present invention (hereinafter, referred to as an inventive inspection apparatus) and the conventional scanning electron microscope (hereinafter, referred-to as a SEM) will be described.

The SEM is used for observing a restricted region, for example, of several tens $\mu$m square at a high magnification for a long time. Even the critical dimension scanning electron microscope (hereinafter, referred to as a CDSEM) as one of semiconductor inspection apparatuses is used for observing and measuring a plurality of restricted points on a wafer at a high magnification. On the contrary, the inventive inspection apparatus is used for searching a defect position on a sample such as a wafer. Accordingly, for the inventive inspection apparatus required to detect a very wide region, the high speed inspection is very important.

Figure 11:
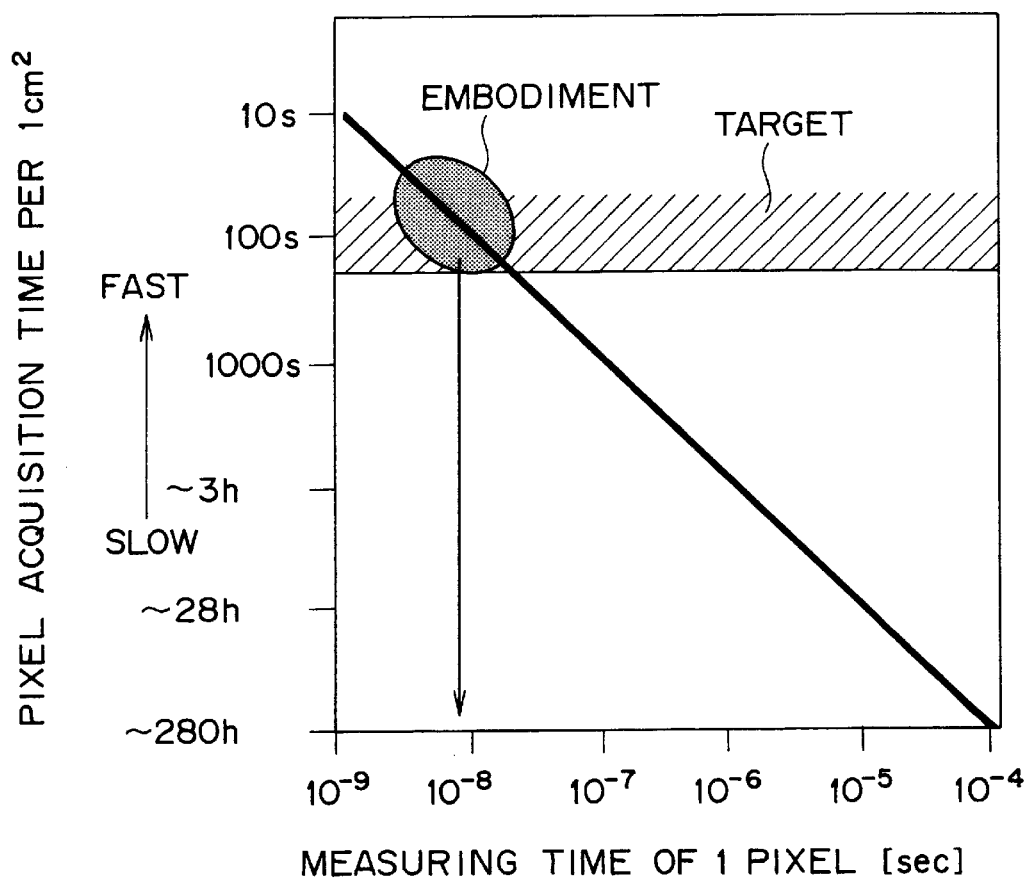
FIG. 11 is a graph showing a relationship between an image acquisition time per 1 $cm^2$ on the surface of a sample and a measurement time for one pixel.

FIG. 11 shows a relationship between an image acquisition time per 1 cm$^2$ and a measuring time for one pixel, and FIG. 12 shows a relationship between an image acquisition time per 1 cm$^2$ and an electron beam current.

In general, the S/N ratio of an electron beam image has a correlation with the root of the number of electrons per unit pixel of an electron beam emitted to irradiate a sample. A defect on the sample to be detected is so minute as to be required to be inspected in the order of pixel, and assuming that the resolution required for the inspection apparatus on the basis of the size of a pattern to be inspected is about 0.1 $\mu$m, the pixel size is about 0.1 $\mu$m. From this view point, and from the experiences of the present inventors, the S/N ratio of a raw image after detection by the charged particle detector and before image processing is desired to be 10 or more. In general, an inspection time required to inspect a circuit pattern on a wafer is about 200 sec/cm$^2$. Assuming that a time required to acquire an image is about a half of the inspection time, that is, about 100 sec/cm$^2$, a measurement time per one pixel becomes 10 nsec or less as shown in FIG. 11 and the number of the necessary electrons per one pixel becomes about 6000. Accordingly, from the data shown in FIG. 12, it is apparent that the electron beam current is required to be 100 nA or more. Additionally, as shown in FIG. 12, since there is no problem even if the image acquisition time per 1 cm$^2$ of the SEM or CDSEM is long, an electron beam current of the SEM or CDSEM is set to be as low as several hundreds pA or less.

Taking into account the above-described circumstances, according to this embodiment, the electron beam current for irradiating a sample is set at 100 nA; the pixel size is set at 0.1 $\mu$m; the spot size of the electron beam on the sample is set at 0.1 $\mu$m or less, specifically, 0.08 $\mu$m; and the continuous moving speed of the sample stage 12 is set at 10 mm/sec. Under these conditions, it is possible to realize a high speed inspection at about 200 sec/cm$^2$ with only one scanning of a region of the sample to be inspected with electron beam.

In the conventional SEM or CDSEM, since the electron beam current for irradiating a sample is in a range of several pA to several hundreds pA, the inspection time per 1 cm$^2$ becomes several hundreds hr, and accordingly, it is substantially impossible to practically use the SEM or CDSEM for inspecting the entire surface of a wafer in the course of the fabrication process thereof.

In this embodiment, to obtain a large current electron beam and to realize high speed inspection, a diffusion supplement type thermal field emission electron source or a Schottky type electron source is used as the electron source 2 of the electron gun 1. Further, the fact that the necessary inspection time per one pixel is 10 nsec means that the frequency of the pixel sampling time is 100 MHz, and accordingly, the charged particle detector 21 is required to have a high speed of response corresponding thereto. To satisfy such a requirement, it is desirable to use a semiconductor detector as the charged particle detector 21.

A sample having a small conductivity or no conductivity is charged by irradiation with an electron beam. The charged amount of the sample is dependent on the acceleration voltage of an electron beam, and more specifically, it can be reduced by lowering the acceleration voltage of the electron beam. However, in the inspection apparatus using an electron beam based on comparison between images, since a large current electron beam of 100 nA is used, if the acceleration voltage is reduced, aberration, that is, the extension of the electron beam in the radial direction is increased by space charge effect, so that it is difficult to form an electron beam spot size of 0.08 $\mu$m on the sample, and accordingly, the resolution is necessarily reduced.

Figure 13:
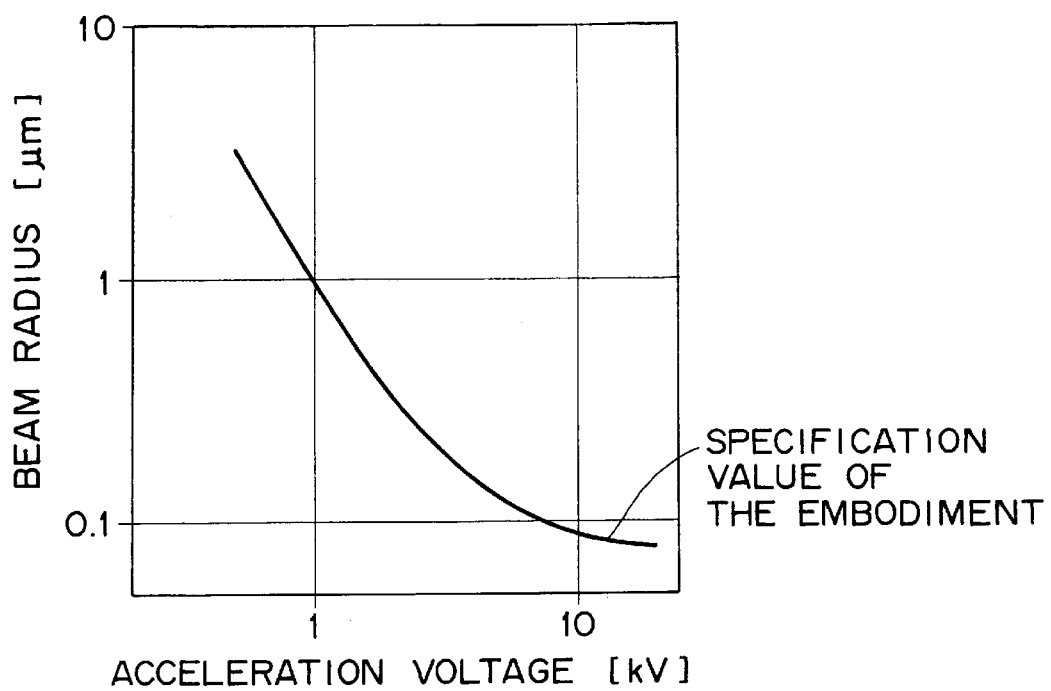
FIG. 13 is a graph showing a relationship between an electron beam radius and an acceleration voltage.

FIG. 13 shows a relationship between the electron beam radius and the acceleration voltage under a condition in which the beam current is set at 100 nm and the sample irradiation energy is set at 0.5 keV. In this embodiment, to prevent the reduction and change in resolution due to space charge effect and to make stable the electron beam spot size of 0.08 $\mu$m on the sample, the acceleration voltage Vacc is set at a constant value of 10 kV as shown in FIG. 13.

The quality of an image obtained by the inventive inspection apparatus is largely dependent on the energy of an electron beam emitted to irradiate a sample. The energy is changed depending on the kind of sample. In the case of a sample difficult to be charged or a sample having a circuit pattern whose edge portion is intended to be inspected by emphasizing the contrast of an image, the energy of the electron beam is made large. Meanwhile, for a sample easy to be charged, the energy of the electron beam is made small. Accordingly, it is required to find out and set the optimal irradiation energy of the electron beam for each change in kind of the sample.

In this embodiment, the optimal irradiation energy of an electron beam emitted to irradiate the sample 13 is set by changing a negative voltage, that is, the retarding voltage applied to the sample 13 without changing the acceleration voltage. The retarding voltage can be changed by adjusting the variable deceleration power supply 14.

Figure 14:
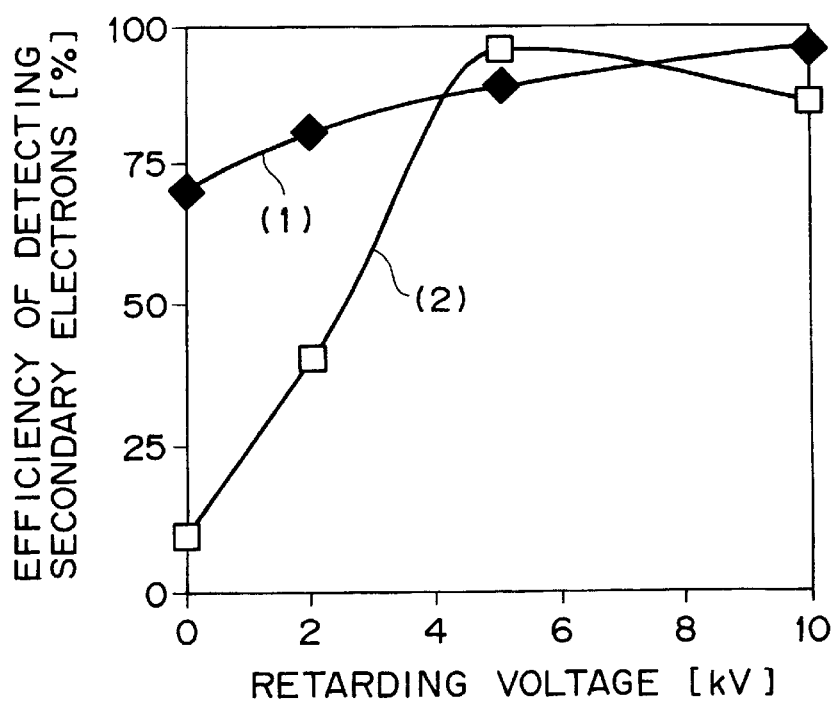
FIG. 14 is a graph showing a relationship between the efficiency of detecting secondary electrons and the retarding voltage.

FIG. 14 shows a relationship between the efficiency (unit: %) of detecting secondary electrons and the retarding voltage (unit: kV). In the figure, the curve (1) shows the characteristic of the long-focal distance method in this embodiment, and the curve (2) shows the characteristic of the TTL type. As described above, the retarding voltage should be changed depending on the kind of sample. The retarding voltage also acts to accelerate secondary electrons. Referring to FIG. 14, in the case of the TTL type, when the retarding voltage is changed, the efficiency of detecting secondary electrons is significantly changed; while in the case of the long-focal distance method in this embodiment, when the retarding voltage is changed, the efficiency of detecting secondary electrons is not changed so much. In the TTL type, the retarding voltage is required to be 5 kV or more. According to the TTL type, secondary electrons generated from a sample are converged after passing through the magnetic field of the objective lens, and the axial converged position of the secondary electrons varies by changing the retarding voltage. This is the main cause of largely changing the efficiency of detecting secondary electron. On the contrary, in the long-focal distance method in this embodiment, since the secondary electrons 33 do not pass through the magnetic field of the objective lens 9, and therefore they are less affected by the magnetic field. Accordingly, in the long-focal distance method in this embodiment, the rotation of an image is small and the variation in efficiency of detecting secondary electrons is small, to thereby stabilize the inspected image.

As described above, the secondary electrons 33 generated from the sample 13 are spread as they are; however, since the secondary electrons 33 are accelerated by the retarding voltage to be nearly collimated, so that the efficiency of collecting the secondary electrons 33 is improved. The secondary electrons 33 are then deflected at an angle, for example, 50 with respect to the center axis of the electron beam 36 by the deflection electric field and the deflection magnetic field of the EXB deflector 18 to be bombarded with the secondary electron generator 19, whereby a large amount of the secondary electrons 20 are generated from the secondary electron generator 19. In this way, the efficiency of the detecting the secondary electrons is significantly improved by collimation of the secondary electrons and bombardment of the secondary electrons with the secondary electron generator 19.

In the TTL type, the charged particles generated from the sample 13 are detected after passing through the objective lens 9. According to the TTL type, since the focal distance of the objective lens is short, it is possible to reduce the aberration and enhance the resolution. On the contrary, in this embodiment, as shown in FIG. 1, the charged particles generated from the sample 13 are detected under the objective lens 9, and accordingly, the focal distance of the objective lens 9 is set to be longer than that in the TTL type. To be more specific, the focal distance of the objective lens in the TTL type is set at about 5 mm, while the focal distance of the objective lens 9 in this embodiment is set at about 40 mm. In this embodiment, to reduce the aberration of an electron beam, as described above, a high acceleration voltage of 10 kV is adopted.

According to this embodiment, the deflection width of the electron beam 36, that is, the scanning-width by the electron beam 36 for acquiring an image of the sample can be set at a large value. For example, the beam deflection width in the conventional TTL method is about 100 μm, while the beam deflection width in this embodiment can be set at 500 μm.

Since the surface of the sample 13 is not perfectly flat, when a region to be inspected is moved, the height of the sample is changed. Accordingly, it is required to usually focus the electron beam on the surface of the sample 13 by changing the excitation of the objective lens 9. In the conventional TTL method, the objective lens is strongly excited to act with its short focal distance usually kept. In the case of the objective lens strongly excited, the flow of an electron beam exhibits rotation toward the horizontal direction accompanied by a change in height of the sample, to cause rotation of the acquired image, so that it is required to correct the rotation of the image. On the other hand, in this embodiment, the objective lens 9 is weakly excited to act with its long focal distance usually kept. For example, the objective lens 9 in this embodiment is excited to such an extent as to be expressed by an equation of $IN/\sqrt{E}$ (for example, about 9) where I designates the current value (unit: A) flowing in the objective lens; N is the turn of the coil of the objective lens; and E is the energy (unit: eV) of the electron beam. Accordingly, even when the focal point is finely adjusted depending on the height of the sample 13, the rotation of the electron beam and the rotation of the acquired image occur only in amounts being too small to be substantially negligible, with a result that it is possible to eliminate the necessity of correcting the rotation of the electron beam.

In the above embodiment, the secondary electrons 33 generated from the sample 13 are used for forming an image; however, reflected electrons backward scattered from the sample by irradiation of the electron beam 36 may be used for forming an image. In this case, the same effect as that described above can be obtained.

Figure 15:
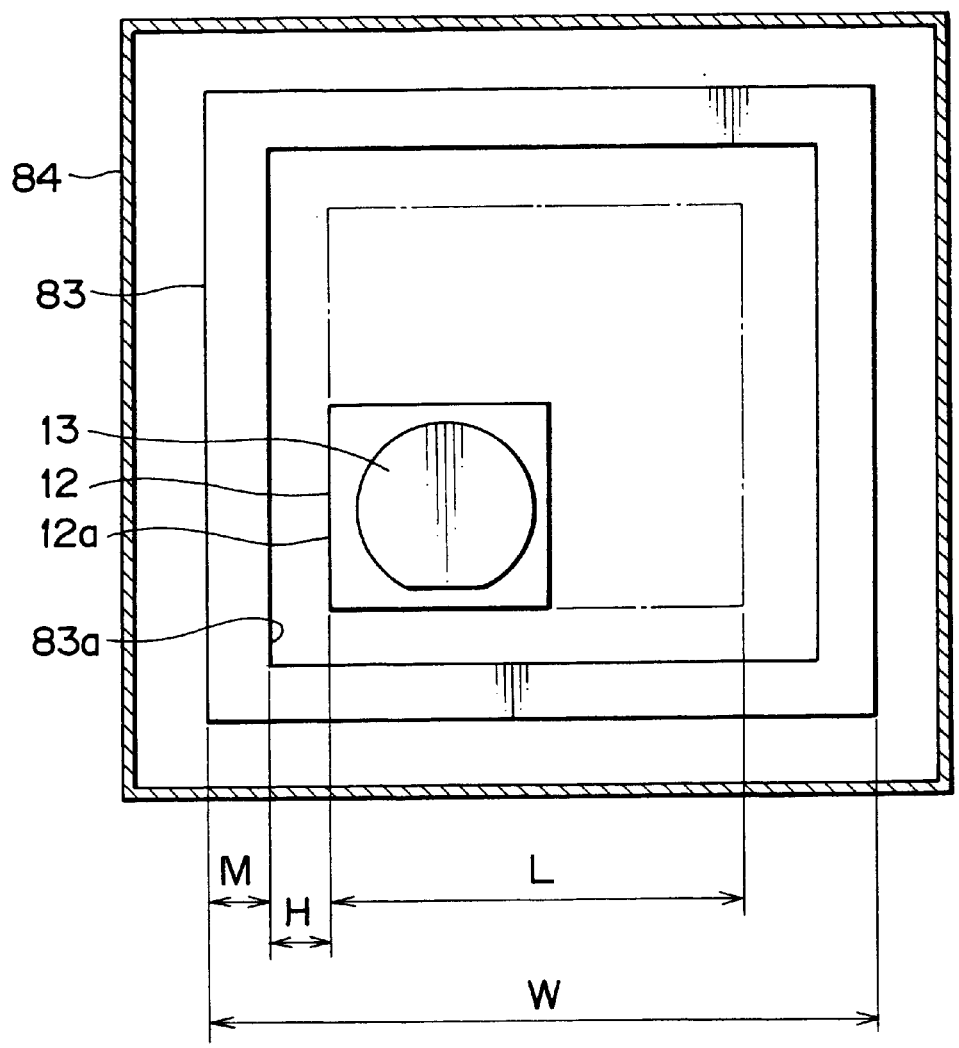
FIG. 15 is a transverse sectional view showing a sample stage and its neighborhood in a chamber.

As described with reference to FIGS. 13 and 14, the retarding voltage should be changed depending on the kind of sample. In this embodiment, when the sample irradiation energy is set at 0.5 keV and the acceleration voltage is set at 10 kV, the retarding voltage is set at 9.5 kV. The retarding voltage is applied to the sample 13 via the sample stage 12 by the variable deceleration power supply 14 shown in FIG. 1. FIG. 15 is a transverse sectional view of the sample stage 12 and its neighborhood in the chamber 43 shown in FIG. 1. The movement range of the sample stage 12 is shown by the alternate long and short dash line. As shown in FIG. 15, the sample stage 12 to which the retarding voltage of 9.5 kV is applied is contained inside an earthed shield frame 83 disposed in the chamber 43. In this case, if the shield frame 83 is excessively closer to the sample stage 12, a discharge occurs therebetween, to degrade the effect of the retarding voltage and to cause disturbance of the electric field on the surface of the sample 13 and noise.

Figure 16:
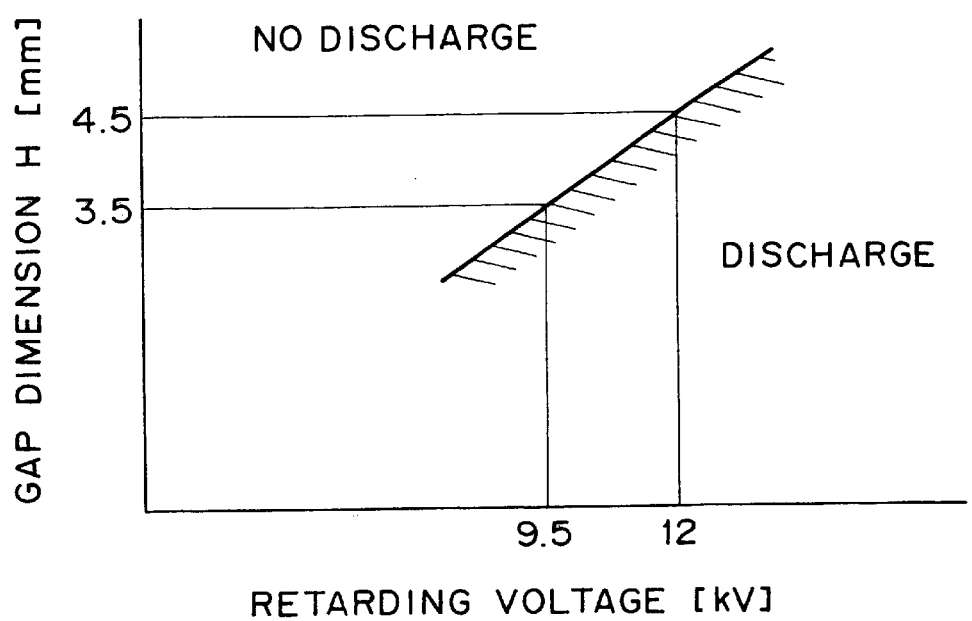
FIG. 16 is a graph showing a relationship between the gap dimension and the retarding voltage with a critical discharge simulated by calculation taken as a parameter.

FIG. 16 shows the result of simulating, by calculation, the critical discharge of part of the sample stage 12 shown in FIG. 15. In the figure, the abscissa designates the retarding voltage, and the ordinate designates a gap dimension H between an end portion 12a of the sample stage 12 and an end portion 83a of the shield frame 83 disposed in the chamber 43. Referring to FIG. 16, when the retarding voltage is set at 9.5 kV specified in this embodiment, the discharge occurring between the end portion 12a of the sample stage 12 and the end portion 83a of the shield frame 83 can be prevented if the gap dimension H therebetween shown in FIG. 15 is set at a value of 3.5 mm or more. In actual design of the inspection apparatus, the gap dimension is set to be larger than the gap dimension H corresponding to occurrence the critical discharge. In this embodiment, the upper limit of the retarding voltage applied to the sample stage 12 is set at 12 kV. In this case, the gap dimension H becomes 4.5 mm from the linear relationship shown in FIG. 16. That is to say, a margin of 1 mm is given to the limited value of 3.5 mm.

As a result of above simulation, it can be assumed that the gap dimension H is 4.5 mm. In this case, referring to FIG.

15, by setting the movement dimension L of the sample stage 12 on which a wafer having a diameter of 300 mm can be mounted at 1141 mm and also setting the width of the shield frame 83 at 35 mm from the viewpoint of strength, the width W of the chamber 43 in which the sample stage 12 is assembled becomes 1220 mm. In actual, since the shield frame 83 is not exposed but is surrounded by a wall 84 having a thickness of about 40 mm, the actual outer dimension of the inspection apparatus becomes larger than the width W (1220 mm) by a dimension equivalent to 80 mm, that is, 1300 mm.

The size of the sample stage is changed depending on the size of a wafer to be mounted thereon, and the movement dimension of the sample stage 12 is also changed. In the case of a wafer having a diameter of 200 mm, the movement length of the sample stage 12 becomes 941 mm, so that the width W of the chamber 43 in which the sample stage 12 is to be assembled becomes 1020 mm and the outer dimension of the inspection apparatus becomes 1100 mm.

In this way, according to this embodiment, since the gap dimension H capable of preventing a discharge occurring between the end portion 12a of the sample stage 12 and the end portion 83a of the shield frame 83 in the chamber 43 is specified, the outer dimension of the inspection apparatus is made as small as possible. In this embodiment, the minimum outer dimension W of a portion, surrounded by the shield frame 83, of the inspection apparatus capable of preventing occurrence of discharge is set at 1220 mm when the diameter of a wafer is 300 mm, and is set at 1020 mm when the diameter of a wafer is 200 mm.

The sample stage 12 is movable in the two-dimensional directions, and the movement amount of the sample stage 12 can be measured by the position monitoring/critical dimension measuring device 11 as shown in FIG. 1. In such measurement by the position monitoring/critical dimension measuring device 11, the interferometer by making use of a laser beam is used, in which a fine movement amount of the sample stage 12 is measured by making a laser beam incident on a mirror mounted on the sample stage 12, and detecting the reflected laser beam by making use of interference of light.

Figure 17:
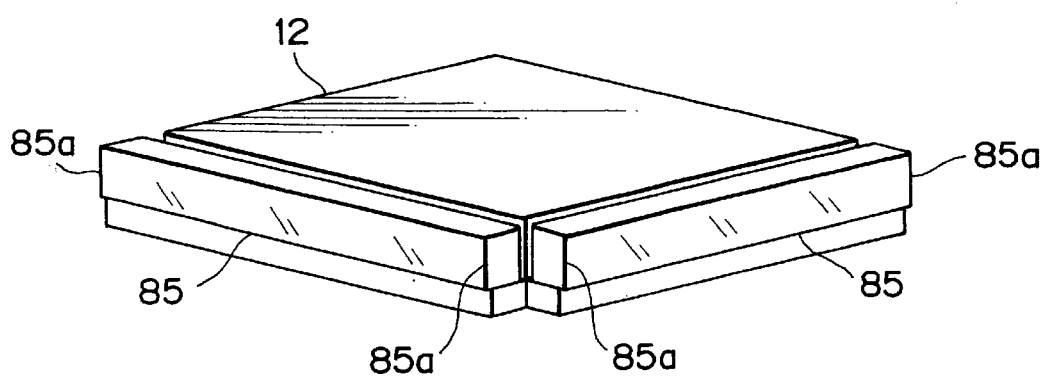
FIG. 17 is a perspective view of a sample stage.
Figure 18:
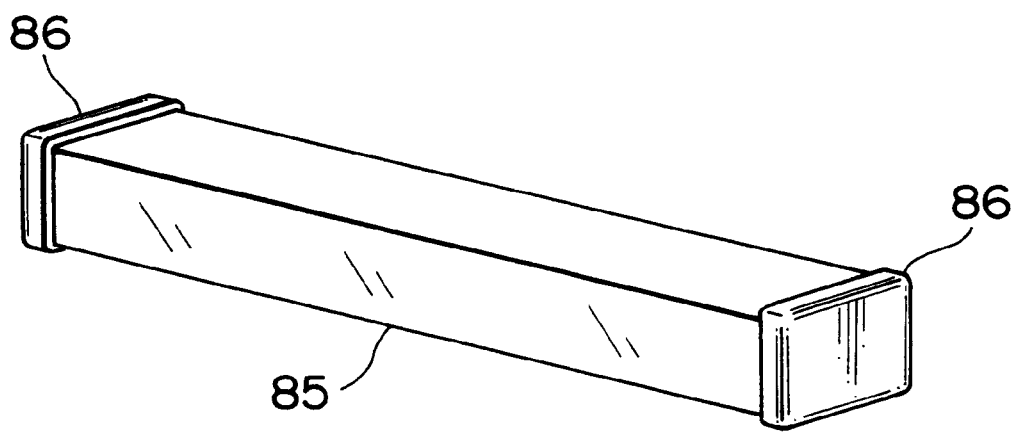
FIG. 18 is a perspective view of a mirror.

FIG. 17 is a perspective view of the sample stage 12 on which mirrors 85 are mounted, and FIG. 18 is a perspective view of the mirror 85. Since the mirror 85 is made from glass, when a retarding voltage is applied to the sample stage 12, an electric field is concentrated at an end portion 85a of the mirror 85, giving rise to a problem that a discharge occurs between the end portion 85a and another earthed member such as the shield frame 83. To cope with such a problem, as shown in FIG. 18, the end portion 85a is covered with a metal cover. With this configuration, it is possible to prevent concentration of the electric field at the end portion 85a, and hence to prevent occurrence of a discharge between the end portion 85a and another earthed member.

As described above, it is possible to prevent occurrence of a discharge at the sample stage to which a retarding voltage is applied and also prevent occurrence of a discharge at the mirror and hence to minimize the inspection apparatus. This makes it possible to easily dispose the inventive inspection apparatus in a restricted clean room in a semiconductor fabrication system.

As described above, according to the present invention, it is possible to obtain an inspection method using an electron beam and an inspection apparatus therefor, which are capable of enhancing the inspection speed and the reliability and also miniaturizing the inspection apparatus.

What is claimed is:

1. An inspection method for inspecting patterns of a semiconductor device with an electron beam, comprising the steps of:

setting a sample on a stage surrounded by a shield frame, wherein a distance between said stage and said shield frame is decided based on a limit of an electric discharge causing between said stage and said shield frame;

applying an electric voltage to said sample through said stage;

scanning an electron beam on said sample;

continuously moving said stage during scanning the electron beam; and detecting a defect relating to detecting charged particles emanating from said sample.

2. An inspection method for inspecting patterns of a semiconductor device with an electron beam according to claim 1, wherein a outside size of said shield frame is decided based on said distance between said stage and said shield frame, which is decided based on a limit of an electric discharge occurring between said stage and said shield frame, a moving distance of said stage and a width of a portion of said shield frame.

3. An inspection method for inspecting patterns of a semiconductor device with an electron beam according to claim 2, wherein said outside size is more than 1020 milli-meters and less than 1300 milli-meters.

4. An inspection method for inspecting patterns of a semiconductor device with an electron beam, comprising the steps of:

setting a sample on a stage;

applying an electric voltage to said sample through said stage;

scanning an electron beam on said sample;

moving said stage while scanning the electron beam;

detecting a defect by detecting charged particles emanating from said sample;

wherein a magnitude of said electric voltage is decided based on the nature of said sample.

5. An inspection method for inspecting patterns of a semiconductor device with an electron beam, comprising the steps of:

scanning an electron beam on a sample;

moving said sample while scanning the electron beam to inspect said patterns;

detecting a defect by detecting charged particles emanating from said sample;

wherein sectional shape of said electron beam is corrected by an electrode having at least six pole coils.

6. An inspection method for inspecting patterns of a semiconductor device with an electron beam, comprising the steps of:

scanning an electron beam on a sample;

moving said sample while scanning the electron beam;

detecting a defect by detecting charged particles emanated from said sample;

wherein said electron beam is blanked so that a cross-over point of said electron beam is a fulcrum of blanking said electron beam.

7. An inspection method for inspecting patterns of a semiconductor device with an electron beam according to claim 6, wherein said detected charged particles are changed to an electric signal, information included in said electric signal is stored in a memory, and said information is used for said detecting said defect.

8. An inspection method for inspecting patterns of a semiconductor device with an electron beam, comprising the steps of:

scanning an electron beam on a first area of a sample;

moving said sample during said scanning of said electron beam on said first area of said sample;

detecting first charged particles emanated from said first area of said sample;

converting said detected first charged particles to a first electric signal;

storing first information included in said first electric signal;

scanning said electron beam on a second area of said sample;

moving said sample during said scanning of said electron beam on said second area of said sample;

detecting second charged particles emanated from said second area of said sample;

converting said detected second charged particles to a second electric signal;

storing second information included in said second electric signal;

comparing said first information with said second information;

detecting a defect in accordance with a result of said comparing step;

wherein said electron beam is blanked so that a cross-over point of said electron beam is a fulcrum of blanking.

9. Inspection apparatus for inspecting patterns of a semiconductor device with an electron beam, comprising:

an electron source generating an electron beam;

a convergence lens converging said electron beam onto a sample;

a stage disposing said sample and moving continuously during scanning said electron beam on said sample;

an electric voltage applying unit applying an electric voltage to said sample through said stage;

a detector detecting a defect by detecting charged particles emanating from said sample scanned by said electron beam;

a shield frame surrounding said stage; and a distance between said stage and said shield frame decided based on a limit of an electric discharge occurring between said stage and said shield frame.

10. Inspection apparatus for inspecting patterns of a semiconductor device with an electron beam according to claim 9, wherein an outside size of said shield frame is decided by factors including at least said distance between said stage and said shield frame, moving distance of said stage and a width of a portion of said shield frame.

11. Inspection apparatus for inspecting patterns of a semiconductor device with an electron beam according to claim 10, wherein said outside size of said shield frame is more than 1020 milli-meters and less than 1300 milli-meters.

12. Inspection apparatus for inspecting patterns of a semiconductor device with an electron beam, comprising:

an electron source generating an electron beam;

a convergence lens converging said electron beam onto a sample;

a stage on which said sample is disposed, said stage moving continuously during scanning of said electron beam on said sample;

an electric voltage supplying unit supplying an electric voltage to said sample through said stage;

a detector detecting a defect by detecting charged particles emanating from said sample by scanning said electron beam;

wherein a magnitude of said electric voltage is decided based on the nature of said sample.

13. Inspection apparatus for inspecting patterns of a semiconductor device with an electron beam, comprising:

an electron source generating an electron beam;

a convergence lens converging said electron beam onto a sample;

a stage disposing said sample and moving continuously during scanning said electron beam on said sample;

an electric voltage supplying unit supplying an electric voltage to said sample through said stage;

a measure having a mirror reflecting a light for measuring a distance of moving said stage and measuring a distance of moving said stage;

a detector detecting a defect by detecting charged particles emanating from said sample by scanning said electron beam;

wherein a metal cover is disposed on a side portion of said mirror.

14. Inspection apparatus for inspecting patterns of a semiconductor device with an electron beam, comprising:

an electron source generating an electron beam;

an electrode having at least six pole coils correcting a sectional shape of said electron beam;

a convergence lens converging said electron beam onto a sample;

a stage on which said sample is disposed, said stage moving continuously during scanning of said electron beam on said sample to inspect said patterns; and.

a detector detecting a defect by detecting charged particles emanating from said sample by scanning said electron beam.

15. An inspection method for inspecting patterns of a semiconductor device with an electron beam, comprising:

an electron source generating an electron beam;

a convergence lens converging said electron beam onto a sample;

a stage on which said sample is disposed, said stage moving continuously during scanning said electron beam on said sample;

an electrode blanking said electron beam so that a cross-over point of said electron beam is a fulcrum of blanking; and a detector detecting a defect by detecting charged particles emanating from said sample by scanning said electron beam.

16. Inspection apparatus for inspecting patterns of a semiconductor device with an electron beam according to claim 15, further comprising a memory storing an information obtained by detecting said charged particles, and wherein said detector detects said defect based on said stored information.

17. Inspection apparatus for inspecting patterns of a semiconductor device with an electron beam, comprising:

an electron source generating an electron beam;

a convergence lens converging said electron beam onto a sample;

a stage on which said sample is disposed, said stage moving continuously during scanning of said electron beam on said sample;

a memory storing first information obtained by detecting first charged particles emanating from a first area of said sample scanned by said electron beam;

a comparator comparing said first information stored in said memory with second information obtained by detecting second charged particles emanating from a second area of said sample scanned by said electron beam; and a detector detecting a defect based on a result of comparing at said comparator, wherein said electron beam is blanked so that a cross-over point of said electron beam is a fulcrum of blanking.

* * * * *